United States Patent [19]

Wojtowicz

[11] 4,090,023

[45] * May 16, 1978

[54] PRODUCTION OF ALKALI METAL SALTS OF DICHLOROISOCYANURIC ACID

[75] Inventor: John A. Wojtowicz, Chesire, Conn.

[73] Assignee: Olin Corporation, New Haven, Conn.

[*] Notice: The portion of the term of this patent subsequent to May 17, 1994, has been disclaimed.

[21] Appl. No.: 710,080

[22] Filed: Jul. 30, 1976

[51] Int. Cl.$^2$ ............................................ C07D 251/36
[52] U.S. Cl. .................................................... 544/190
[58] Field of Search ..................... 260/248 C; 544/190

[56] References Cited

U.S. PATENT DOCUMENTS

| | | | |
|---|---|---|---|
| 2,956,056 | 10/1960 | Christain | 260/248 |
| 3,668,204 | 6/1972 | Mesiah | 260/248 C |
| 3,835,135 | 9/1974 | Sawhill | 260/248 C |
| 3,896,213 | 7/1975 | Mirdler | 260/248 |
| 4,024,140 | 5/1977 | Wojtowicz | 260/248 |

Primary Examiner—John M. Ford
Attorney, Agent, or Firm—James B. Haglind; Donald F. Clements; Thomas P. O'Day

[57] ABSTRACT

Alkali metal salts of dichloroisocyanuric acid are produced by the reaction of a monoalkali metal cyanurate with an alkali metal hypochlorite and chlorine in an aqueous medium while maintaining the pH of the reaction mixture in the range of from about 6.0 to about 7.5 and recovering the solid alkali metal dichloroisocyanurate produced thereby.

The products are useful as bleaching or sanitizing agents.

6 Claims, No Drawings

PRODUCTION OF ALKALI METAL SALTS OF DICHLOROISOCYANURIC ACID

This invention relates to a process for producing salts of dichloroisocyanuric acid. More particularly, this invention relates to a process for producing alkali metal dichloroisocyanurates. These compounds are well-known products used in laundry, bleaching and sanitizing applications.

It is known to produce alkali metal salts of dichloroisocyanuric acid by reacting a dilute solution of trisodium or tripotassium cyanurate with chlorine, as described in U.S. Pat. No. 3,035,056, issued May 15, 1962, to W. F. Symes. This process produces large amounts of sodium chloride or potassium chloride as a by-product. Copious amounts of water are employed to keep the alkali metal chloride in solution and prevent it from contaminating the alkali metal dichloroisocyanurate product. The water content of the reaction mixture is in excess of 70 percent of the weight of the mixture. A multi-step procedure is employed to recover an alkali metal dichloroisocyanurate product from large volumes of alkali metal chloride solution which must be disposed of. In addition, the product of the trisodium or tripotassium cyanurate starting material requires superfluous amounts of base, increasing the material costs of the process.

There is need at the present time for an improved process for the preparation of alkali metal salts of dichloroisocyanuric acid.

It is an object of the present invention to provide a process for producing alkali metal salts of dichloroisocyanuric acid having reduced amounts of by-product-containing waste solutions.

Another object of the present invention is to provide a process for the production of alkali metal salts of dichloroisocyanuric acid employing a monoalkali metal cyanurate.

A further object of the present invention is a process for producing alkali metal salts of dichloroisocyanuric acid in which the production of alkali metal chloride is significantly reduced.

These and other objects of the invention will be apparent from the following description of the invention.

Briefly, the foregoing objects are accomplished in a process for the production of alkali metal salts of dichloroisocyanuric acid which comprises reacting a monoalkali metal cyanurate with an alkali metal hypochlorite and chlorine in an aqueous medium to form a reaction mixture containing the alkali metal salt of dichloroisocyanuric acid and an alkali metal chloride, and recovering the alkali metal salt of dichloroisocyanuric acid.

More in detail, any monoalkali metal cyanurate such as monosodium, monopotassium, or monolithium cyanurate can be reacted in accordance with the process of this invention. A preferred embodiment is the use of monosodium cyanurate. While the monoalkali metal cyanurate may be reacted as a solid, it is preferred that an aqueous slurry of the monoalkali metal cyanurate be employed as a reactant. For example, the aqueous slurry should be at such a concentration that it can be pumped or conveyed under the reaction conditions employed and yet not be so diluted than an excessive amount of water must be handled. An aqueous slurry of monoalkali metal cyanurate containing from about 10 to about 50 percent, preferably from about 12 to about 35 percent of solid cyanurate is suitable.

Suitable alkali metal hypochlorites include, for example, sodium, potassium, and lithium hypochlorites, with sodium hypochlorite being preferred. Aqueous solutions containing from about 5 to about 35, and preferably from about 10 to about 20 percent by weight of alkali metal hypochlorite may be employed.

The reaction of the process of the present invention is believed to proceed according to the following equation in which monosodium cyanurate is used as the monoalkali metal cyanurate and sodium hypochlorite as the alkali metal hypochlorite.

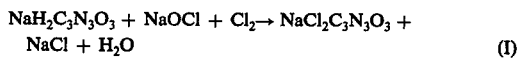

$$NaH_2C_3N_3O_3 + NaOCl + Cl_2 \rightarrow NaCl_2C_3N_3O_3 + NaCl + H_2O \qquad (I)$$

The feed rates of the monoalkali metal cyanurate, alkali metal hypochlorite and chlorine are adjusted to maintain the pH of the reaction mixture at from about 6.0 to about 7.5 and preferably at from about 6.2 to about 7.0.

The reaction is generally carried out using about stoichiometric proportions of the reactants. As illustrated, for example, by Equation (I) above, the molar ratio of monoalkali metal cyanurate to either the alkali metal hypochlorite or to chlorine is about 1:1. An excess of chlorine may be used if desired to assure that the complete conversion of the monoalkali metal cyanurate to the alkali metal dichloroisocyanurate takes place.

The reaction temperature is suitably maintained at from about 0° C. to about 50° C., and preferably at from about 10° C. to about 35° C.

An aqueous slurry or solution is produced containing a hydrate of the alkali metal dichloroisocyanurate in admixture with a solution of the alkali metal chloride. The hydrate of the alkali metal dichloroisocyanurate may be recovered by any suitable means such as filtering and drying the filter cake.

When monosodium or monolithium cyanurate are the reactants, sodium dichloroisocyanurate dihydrate and lithium dichloroisocyanurate dihydrate are the reaction products respectively while monopotassium cyanurate produces potassium dichloroisocyanurate monohydrate. Heating the hydrated salt products to the appropriate temperature will form the anhydrous salt or monohydrate, as desired. For example, heating sodium dichloroisocyanurate dihydrate to a temperature in the range of from about 60° C to about 90° C forms sodium dichloroisocyanurate monohydrate. Heating the dihydrate to a temperature above about 90° C. preferably in the range of from about 95° C to about 110° C produces anhydrous sodium dichloroisocyanurate.

The process and composition of the present invention are further illustrated by the following examples. All percentages used are by weight unless otherwise specified.

EXAMPLE

Monosodium cyanurate monohydrate (16.9 g, 0.1 m.) was mixed with 65 mls. of water and the slurry, containing 21 percent solids, was pumped to a chlorinator. Simultaneously added to the chlorinator was gaseous chlorine (7.1 g, 0.1 m.) and 57.3 g (0.1 m.) of a 13 percent aqueous solution of sodium hypochlorite. The controlled addition of the reactants over a 30-minute period maintained the pH of the reaction mixture at 6.5 ± .2. A reaction temperature of about 15° was maintained by circulating cooling water through a jacket surrounding the chlorinator. During the reaction period, the reaction mixture was agitated. Filtration of the reaction mixture occured rapidly and the filter cake, containing about 30 percent water, was air dried and then oven dried to give 13.8 grams of anhydrous sodium dichloroisocyanurate containing 5.1 percent sodium chloride and having an available chlorine content of about 60 percent.

What is claimed is:

1. A process for the production of alkali metal salts of dichloroisocyanuric acid which comprises reacting a monoalkali metal cyanurate with an alkali metal hypochlorite and chlorine in an aqueous medium while maintaining a pH of from about 6.0 to about 7.5 to form a reaction mixture containing said alkali metal salt of dichloroisocyanuric acid and an alkali metal chloride, and recovering said alkali metal salt of dichloroisocyanuric acid.

2. The process of claim 1 in which said monoalkali metal cyanurate is an aqueous slurry which contains from about 10 to about 50 percent by weight of said monoalkali metal cyanurate.

3. The process of claim 2 in which said reaction mixture is maintained at a temperature of from about 0° to about 50° C.

4. The process of claim 2 in which said monoalkali metal cyanurate is monosodium cyanurate and said alkali hypochlorite is sodium hypochlorite.

5. The process of claim 4 in which said monoalkali metal cyanurate is an aqueous slurry of monosodium cyanurate containing from about 12 to about 35 percent by weight of monosodium cyanurate.

6. The process of claim 5 in which the pH of said reaction mixture is maintained at from about 6.2 to about 7.0.

* * * * *